United States Patent
Letsinger et al.

(10) Patent No.: US 6,602,669 B2
(45) Date of Patent: Aug. 5, 2003

(54) METHOD OF DETECTION BY ENHANCEMENT OF SILVER STAINING

(75) Inventors: Robert L. Letsinger, Wilmette, IL (US); Viswanadham Garimella, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/903,461

(22) Filed: Jul. 11, 2001

(65) Prior Publication Data

US 2002/0034756 A1 Mar. 21, 2002

Related U.S. Application Data (60) Provisional application No. 60/217,782, filed on Jul. 11, 2000.

(51) Int. Cl.[7] .................. C12Q 1/68; C07M 21/04; G01N 33/20; G01N 21/00; G01N 21/75
(52) U.S. Cl. ..................... 435/6; 536/24.3; 436/73; 436/80; 436/164
(58) Field of Search ............... 435/6; 536/24.3; 436/73, 80, 164

(56) References Cited

U.S. PATENT DOCUMENTS

| | | | |
|---|---|---|---|
| 4,193,983 A | 3/1980 | Ullman et al. | |
| 4,256,834 A | 3/1981 | Zuk et al. | |
| 4,261,968 A | 4/1981 | Ullman et al. | |
| 4,313,734 A | 2/1982 | Leuvering | |
| 4,318,707 A | 3/1982 | Litman et al. | |
| 4,650,770 A | 3/1987 | Liu et al. | |
| 4,713,348 A | 12/1987 | Ullman | |
| 4,853,335 A | 8/1989 | Olsen et al. | |
| 4,868,104 A | 9/1989 | Kurn et al. | |
| 5,225,064 A | 7/1993 | Henkens et al. | |
| 5,284,748 A | 2/1994 | Mroczkowski et al. | |

(List continued on next page.)

FOREIGN PATENT DOCUMENTS

| EP | 0 630 974 A2 | 12/1994 |
|---|---|---|
| EP | 0 667 398 A2 | 8/1995 |
| WO | WO 89/06801 | 7/1989 |

(List continued on next page.)

OTHER PUBLICATIONS

Stimpson, et al., "Real–time detection of DNA hybridization and melting on oligonucleotide arrays by using optical wave guides," *Proc. Natl. Acad. Sci.*, vol. 92, pp. 6379–6383, California Institute of Technology (1995) U.S.

(List continued on next page.)

*Primary Examiner*—Kenneth R. Horlick
*Assistant Examiner*—Teresa E Strzelecka
(74) *Attorney, Agent, or Firm*—McDonnell Boehnen Hulbert & Berghoff (57) ABSTRACT

The present invention relates to a method for amplifying a detection signal by enhancing or promoting the deposition of additional silver in assay detection systems where the formation of a silver spot serves as a reporter for the presence of a target molecule, including biological polymers (e.g., proteins and nucleic acids) and small molecules.

30 Claims, 2 Drawing Sheets

U.S. PATENT DOCUMENTS

| | | | |
|---|---|---|---|
| 5,288,609 A | 2/1994 | Engelhardt et al. | |
| 5,294,369 A | 3/1994 | Shigekawa et al. | |
| 5,360,895 A | 11/1994 | Hainfeld et al. | |
| 5,384,073 A | 1/1995 | Shigekawa et al. | |
| 5,384,265 A | 1/1995 | Kidwell et al. | |
| 5,460,831 A | 10/1995 | Kossovsky et al. | |
| 5,472,881 A | 12/1995 | Beebe et al. | |
| 5,514,602 A | 5/1996 | Brooks, Jr. et al. | |
| 5,521,289 A | 5/1996 | Hainfeld et al. | |
| 5,543,158 A | 8/1996 | Gref et al. | |
| 5,571,726 A | 11/1996 | Brooks, Jr. et al. | |
| 5,599,668 A | 2/1997 | Stimpson et al. | |
| 5,609,907 A | 3/1997 | Natan | |
| 5,637,508 A | 6/1997 | Kidwell et al. | |
| 5,665,582 A | 9/1997 | Kausch et al. | |
| 5,681,943 A | 10/1997 | Letsinger et al. | |
| 5,751,018 A | 5/1998 | Alvisatos et al. | |
| 5,830,986 A | 11/1998 | Merrill et al. | 528/332 |
| 5,900,481 A | 5/1999 | Lough et al. | 536/55.3 |
| 5,939,021 A | 8/1999 | Hansen et al. | |
| 5,990,479 A | 11/1999 | Weiss et al. | |
| 6,025,202 A | 2/2000 | Natan | |
| 6,149,868 A | 11/2000 | Natan et al. | |
| 6,203,989 B1 | 3/2001 | Goldberg et al. | 435/6 |
| 6,251,303 B1 | 6/2001 | Bawendi et al. | 252/301.4 R |
| 6,277,489 B1 | 8/2001 | Abbott et al. | 428/403 |
| 6,306,610 B1 | 10/2001 | Bawendi et al. | 435/7.1 |
| 6,361,944 B1 | 3/2002 | Mirkin et al. | 435/6 |
| 6,365,418 B1 | 4/2002 | Wagner et al. | 436/518 |
| 6,417,340 B1 | 7/2002 | Mirkin et al. | 536/23.1 |

FOREIGN PATENT DOCUMENTS

| | | |
|---|---|---|
| WO | WO 90/02205 | 3/1990 |
| WO | WO 92/04469 | 3/1992 |
| WO | WO 93/10564 | 3/1993 |
| WO | WO 93/25709 | 12/1993 |
| WO | WO 97/40181 | 10/1997 |
| WO | WO 98/04740 | 2/1998 |
| WO | WO 98/10289 | 3/1998 |
| WO | WO 98/17317 | 4/1998 |
| WO | WO 99/23258 | 10/1998 |
| WO | WO 99/20789 | 4/1999 |
| WO | WO 99/21934 | 5/1999 |
| WO | WO 99/23258 | 5/1999 |
| WO | WO 99/60169 | 11/1999 |
| WO | WO 01/00876 | 4/2001 |
| WO | WO 01/51665 | 7/2001 |
| WO | WO 01/73123 | 10/2001 |
| WO | WO 01/86301 | 11/2001 |
| WO | WO 02/04681 | 1/2002 |
| WO | WO 02/18643 | 3/2002 |
| WO | WO 02/36169 | 5/2002 |
| WO | WO 00/33079 | 6/2002 |
| WO | WO 02/46472 | 6/2002 |
| WO | WO 02/46483 | 6/2002 |

OTHER PUBLICATIONS

Storhoff, et al., "Strategies for Organizing Nanoparticles into Aggregate Structures and Functional Materials," *Journal of Cluster Science*, vol. 8, No. 2, pp. 179–217, Plenum Publishing Corporation (1997) U.S.

Storhoff, et al., "One–Pot Colorimetric Differentiation of Polynucleotides with Single Base Imperfections Using Gold Nanoparticle Probes," *J. Am. Chem. Soc.*, vol. 20, pp. 1961–1964, American Chemical Society (1998) U.S.

Tomlinson, et al., "Detection of Biotinylated Nucleic Acid Hybrids by Antibody–Coated Gold Colloid," *Analytical Biochemistry*, vol. 171, pp. 217–222, Academic Press, Inc. (1988) U.S.

Velev, et al., "In Situ Assembly of Colloidal Particles into Miniaturized Biosensors," *Langmuir*, vol. 15, No. 11, pp. 3693–3698, American Chemical Society (1999) U.S.

Zhu, et al., "The First Raman Spectrum of an Organic Monolayer on a High–Temperature Superconductor: Direct Spectroscopic Evidence for a Chemical Interaction between an Amine and $Yba_2Cu_3O_{7-8}$," *J. Am. Chem. Soc.*, vol. 119, pp. 235–236, American Chemical Society (1997) U.S.

Yguerabide, et al., "Light–Scattering Submicroscopic Particles as Highly Fluorescent Analogs and Their Use as Tracer Labels in Clinical And Biological Applications," I. Theory, *Analytical Biochemistry*, vol. 262, pp. 137–156 (1998) U.S.

Yguerabide, et al. "Light–Scattering Submicroscopic Particles as Highly Fluorescent Analogs and Their Use as Tracer Labels in Clinical and Biological Applications," II. Experimental Characterization, *Analytical Biochemistry*, vol. 262, pp. 157–176 (1998) U.S.

Letsinger, R., et al., "Chemistry of Olgonucleotide–Gold Nanoparticle Conjugates," *Phosphorus, Sulfur and Silicon*, vol. 144, p. 359–362 (1999).

Letsinger, R., et al., "Use of a Steroid Cyclic Disulfide Anchor in Constructing Gold Nanoparticle–Oligonucleotide Conjugates," *Bioconjugate Chem*, p. 289–291 (2000).

Li Z., "Multiple thiol–anchor capped DNA–gold nanoparticle conjugates," *Nucleic Acids Research*, vol. 30, p. 1558–1562 (2002).

Nuzzo R., et al., "Spontaneously Organized Molecular Assemblies. 3. Preparation and Properties of Solution Adsorbed Monolayers of Organic Disulfides on Gold Surfaces," *J. Am Chem. Soc.*, vol. 109, p. 2358–2368 (1987).

Otsuka, H., et al., "Quantitative and Reversible Lectin–Induced Association of Gold Nanoparticles Modified with $\alpha$–Lactosyl–$\omega$–mercapto–poly(ethyleneglycol)," *J. Am Chem. Soc.*, vol. 123, p. 8226–8230 (2001).

Wuelfing, P., "Nanometer Gold Clusters Protected by Surface–Bound Monolayers of Thiolated Poly(ethylene glycol) Polymer Electrolyte," *J. Am Chem. Soc.*, vol. 120, p. 12696–12697 (1998).

Alivisatos et al., "Organization of 'nanocrystal molecules' using DNA," *Nature*, vol. 382, pp. 609–611 (1996).

Bain, et al., "Modeling Organic Surfaces with Self–Assembled Monolayers," *Angew. Chem. Int. Ed. Engl.*, vol. 28, pp. 506–512 (1989).

Bradley, "The Chemistry of Transition Metal Colloids," *Clusters and Colloids: From Theory to Applications*, G. Schmid, Editor, BCH, Weinheim, New York, pp. 459–542 (1994).

Brust et al., "Novel Gold–Dithiol Nano–Networks with Non–Metallic Electronic Properties," *Adv. Mater.*, vol. 7, pp. 795–797 (1995).

Chen et al., "A Specific Quadrilateral Synthesized from DNA Branched Junctions," *J. Am. Chem. Soc.*, vol. 111, pp. 6402–6407 (1989).

Chen & Seeman, "Synthesis from DNA of a molecule with the connectivity of a cube," *Nature*, vol. 350, pp. 631–633 (1991).

Chen et al., Crystal Structure of a Four–Stranded Intercalated DNA: $d(C_4)$*Biochem.*, vol. 33, pp. 13540–13546 (1994).

Dagani, "Supramolecular Assemblies DNA to organize gold nanoparticles," *Chemical & Engineering News*, p. 6–7, Aug. 19, 1996.

Dubois & Nuzzo, "Synthesis, Structure, and Properties of Model Organic Surfaces," *Annu. Rev. Phys. Chem.*, vol. 43, pp. 437–464 (1992).

Elghanian et al., "Selective Colorimetric Detection of Polynucleotides Based on the Distance–Dependent Optical Properties of Gold Nanoparticles," *Scienece*, vol. 277, pp. 1078–1081 (1997).

Grabar et al., "Preparation and Characterization of Au Colloid Monolayers," *Anal. Chem.* vol. 67, pp. 735–743 (1995).

Hacia et al., "Detection of heterozygous mutations in BRCA1 using high density oligonucleotide arrays and two-colour fluorescence analysis," *Nature Genet.*, vol. 14, pp. 441–447 (1996).

Jacoby, "Nanoparticles change color on binding to nucleotide target," *Chemical & Engineering News*, p. 10, Aug. 25, 1997.

Letsinger et al., Use of Hydrophobic Substituents in Controlling Self–Assembly of Oligonucleotides, *J. Am. Chem. Soc.*, vol. 115, pp. 7535–7536 (1993).

Letsinger et al., "Control of Excimer Emission and Photochemistry of Stilbene Units by Oligonucleotide Hybridization," *J. Am. Chem. Soc.*, vol. 116, pp. 811–812 (1994).

Marsh et al., "A new DNA nanostructure, the G–wire, imaged by scanning probe microscopy," *Nucleic Acids Res.*, vol. 23, pp. 696–700 (1995).

Mirkin, "H–DNA and Related Structures," *Annu. Review Biophys. Biomol. Struct.*, vol. 23, pp. 541–576 (1994).

Mirkin et al., "A DNA–based method for rationally assembling nanoparticles into macroscopic materials," *Nature*, vol. 382, pp. 607–609 (1996).

Mirkin et al., "DNA–Induced Assemblu of Gold Nanoparticles: A Method for Rationally Organizing Colloidal Particles into Ordered Macroscopic Materials," *Abstract* 249, Abstracts of Papers Part 1, 212 ACS National Meeting 0–8412–3402–7, American Chemical Society, Orlando, FL, Aug. 25–29, 1996.

Mucic et al., "Synthesis and characterization of DNA with ferrocenyl groups attached to their 5'–termini: electrochemical characterization of a redox–active nucleotide monolayer," *Chem. Commun.*, pp. 555–557 (1996).

Mulvaney, "Surface Plasmon Spectroscopy of Nanosized Metal Particles," *Langmuir*, vol. 12, pp. 788–800 (1996).

Rabke–Clemmer et al., "Analysis of Functionalized DNA adsorption on Au(111) Using Electron Spectroscopy", *Langmuir*, vol. 10, pp. 1796–1800 (1994).

Roubi, "Molecular Machines–Nanodevice with rotating arms assembled from synthetic DNA," *Chemical & Engineering News*, p. 13, (Jan. 18, 1999).

Seeman et al., "Synthetic DNA knots and catenanes,"*New J. Chem.*, vol. 17, pp. 739–755 (1993).

Shaw & Wang, "Knotting of a DNA Chain During Ring Closure," *Science*, vol. 260, pp. 533–536 (1993).

Shekhtman et al., "Stereostructure of replicative DNA catenanes from eukaryotic cells,"*New J. Chem.* vol. 17, pp. 757–763 (1993).

Smith and Feigon, "Quadruplex structure of Oxytrichia telomeric DNA oligonucleotides," *Nature*, vol. 356, pp. 164–168 (1992).

Thein et al., "The use of synthetic oligonucleotides as specific hybridization probes in the diagnosis of genetic disorders," $2^{nd}$ Ed., K.E. Davies, Ed., Oxford University Press, Oxford, New York, Tokyo, p. 21–33 (1993).

Wang et al., "A DNA Aptamer Which Binds to and Inhibits Thrombin Exhibits a New Structural Motif for DNA," *Biochem.*, vol. 32, pp. 1899–1904 (1993).

Wang et al., "Assembly and Characterization of Five–Arm and Six–Arm DNA Branched Junctions," *Biochem.*, vol. 30, pp. 5667–5674 (1991).

Weisbecker et al., "Molecular Self–Assembly of Aliphatic Thiols on Gold Colloids," *Langmuir*, vol. 1, pp. 3763–3772 (1996).

Wells, "Unusual DNA Structures," *J. Biol. Chem.*, vol. 263, pp. 1095–1098 (1988).

Zhang et al., "Informational Lipsomes: Complexes Derived from Cholesteryl–conjugated Oligonucleotides and Liposomes," *Tetrahedron Lett.*, vol. 37, pp. 6243–6246 (1996).

Borman, Chem.Eng. News, Dec. 9, 1996, pp. 42–43 (1996).

Tomlinson et al., *Anal. Biochem*, vol. 171, pp. 217–222 (1998).

O.D. Velev, et al., "In Situ Assembly of Collordal Particles into Miniaturized Biosensors," *Langmuir*, vol. 15, No. 11, pp. 3693–3698, May 25, 1999.

Brada, et al., "Golden Blot"–Detection of Polyclonal and Monoclonal Antibodies Bound to Antigens on Nitrocellulose by Protein A–Gold Complexes, *Analytical Biochemistry*, vol. 42, pp. 79–83 (1984) U.S.

Dunn, et al., A Novel Method to Map Transcripts: Evidence for homology between an Adenovirus mRNA and Discrete Multiple Regions of the Viral Genome, *Cell*, vol. 12, pp. 23–36, (1997) U.S.

Hacker, Higher performance Nanogold–Silver in situ hybridisation, *Eur. J. Histochem*, vol. 42, pp. 111–120 (1998) U.S.

Ranki, et al., Sandwich hybridization as a covenient method for the detection of nucleic acids in crude samples, *Gene*, vol. 21, pp. 77–85 (1983) U.S.

Romano, et al., "An antiglobulin reagent labelled with colloidal gold for use in electron microscopy," *Immunochemistry*, vol. 11, pp. 521–522 (1974) Great Britain.

Bendayan, M., "A Review of the Potential and Versatility of Colloidal Gold Cytochemical Labeling for Molecular Morphology," *Biotechnic & Histochemistry*, vol. 75, pp. 203–242 (2000).

Taton, T., et al., "Scanometric DNA Array Detection with Nanoparticle Probes," *Science*, vol. 289, pp. 1757–1760 (2000).

SEQUENCE LISTING

<160> NUMBER OF SEQ ID NOS: 3

<210> SEQ ID NO 1
<211> LENGTH: 36
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(1)
<223> OTHER INFORMATION: n=HS(CH2)6OP(O)(O)O

<400> SEQUENCE: 1
naaaaaaaaa aaaaaaaaaa atgggtagca gacctc                                36

<210> SEQ ID NO 2
<211> LENGTH: 30
<212> TYPE: DNA
<213> ORGANISM: Artificial Sequence
<220> FEATURE:
<223> OTHER INFORMATION: synthetic oligomer

<400> SEQUENCE: 2
gctctagaat gaacggtgga aggcggcagg                                       30

<210> SEQ ID NO 3
<211> LENGTH: 63
<212> TYPE: DNA
<213> ORGANISM: Artificial Sequence
<220> FEATURE:
<223> OTHER INFORMATION: synthetic oligomer

<400> SEQUENCE: 3
gtaggcgaac cctgcccagg tcgacacata ggtgaggtct gctacccaca gccggttagg      60
tgc                                                                   63

METHOD OF DETECTION BY ENHANCEMENT OF SILVER STAINING

CROSS-REFERENCE

This application claims the benefit of priority from U.S. Provisional application No. 60/217,782, filed Jul. 11, 2000.

FIELD OF THE INVENTION

The invention relates to several fields, especially to the detection of specific nucleic acids, proteins, carbohydrates, or organic compounds immobilized on a solid surface. More particularly it relates to detection systems in which the immobilized target is recognized by a metallic nanoparticle probe and for which the signal for detection has been amplified by reductive deposition of silver on the nanoparticle probe.

BACKGROUND OF THE INVENTION (a) Gold Nanoparticle Probes

The use of gold nanoparticle probes as reporter for detection of biological polymers was first described by W. P. Faulk and G. M. Taylor, who employed the nanoparticles as immunocytochemical probes for surface antigens [*Immunochemitry,* 8, 1081 (1971)]. Since then gold colloids have been widely used for detection of a variety of proteins using electron or light-microscopy to observe the particles [for reviews see Hacker, G. W. in *Colloidal Gold; Principles, Methods, and Applications,* Vol. 1, Academic Press, Inc. (1998) p 297, and Garzon, S., and Bendayan, M. in *Immuno-Gold Electron Microscopy in Virus Diagnosis and Research,* Ed. Hyatt, A. D. and Eaton, B. T., CRC Press, Ann Arbor, (1993) p 137]. Recently, applications of gold nanoparticle or cluster conjugates as probes for detection of oligonucleotides and nucleic acids have been suggested [Kidwell, D. A., and Conyers, S. M., U.S. Pat. No. 5,384,265 (1995); Hainfeld, J. F., et al. U.S. Pat. No. 5,521,289 (1996)] and described [Tomlinson, S., et al., *Analytical Biochemistry,* 171, 217 (1988); Mirkin et al., *Nature,* 15, 607 (1996); Storhoff, J. J. et al., *J. Am. Chem. Soc.,* 120, 1959 (1998)].

(b) Silver Enhancement of Signal

It has been found that the sensitivity for assays utilizing gold markers for proteins in tissues [Danscher, G. *Histochemistry,* 71, 1 (1981); Holgate, C. S. et al. *J. Histochem. Cytochem.* 31, 938 (1983)], for nucleic acids visualized in situ in immobilized biological systems [Gassell, G. J., et al.,*J. Cell Biology,* 126, 863 (1994); Zehbe, I. et al.,*Am J. of Pathology,* 150, 1553 (1997); Hacker, G. W., *Eur. J. Histochem* 42, 111 (1998) and for gold probes targeted to oligonucleotides captured on oligonucleotide arrays on a glass surface [T. A. Taton, C. A. Mirkin, R. L. Letsinger, *Science,* 289, 1757 (2000)] can be significantly increased by silver staining. In this process, the gold particles captured on a surface are treated with a solution containing silver ions and a reducing agent (e.g., hydroquinone). The gold catalyzes reduction of the silver ions so that silver is deposited on the gold particle, and the early-deposited silver can itself catalyze further reduction of silver ion. As a consequence, the amount of metal that can be visualized is greatly increased. Unfortunately, however, the silver reduction catalyzed by the deposited silver ceases after a time, so the extent of amplification achievable is limited. When employed in enhancing visibility of gold nanoparticles on a glass plate, one observes darkening of the spot characteristic for the gold probes captured by a target sequence. Indeed, a good silver spot may be observed for cases where the amount of gold deposited initially is too small to be visible to the naked eye. Typically, the reaction time for the silver staining step is short, of the order of five minutes or less. Long exposure to the silver solution leads to non-selective deposition of silver metal and a high background. The silver ion solution and the reducing agent are mixed just prior to application to minimize the uncatalyzed reduction.

(c) Oligo- and Polynucleotide Arrays

A recent major innovation in biology utilizes arrays of oligonucleotides or polynucleotides tethered to a solid surface. These oligomers serve as capture probes to bind complementary DNA or RNA target sequences. The captured sequences can in turn be recognized by fluorescent labels previously attached to them or by fluorescent or calorimetric probes that bind to a segment of the target. As stated by Eric Lander [*Nature Genetics Supplement,* 21, 3 (1999)]: "Arrays offer the first great hope . . . by providing a systematic way to survey DNA and RNA variation. They seem likely to become a standard tool of both molecular biology research and clinical diagnostics. These prospects have attracted great interest and investment from both the public and private sectors."

Array technology is indeed now greatly accelerating developments in our understanding of genetic variation and gene expression. Nevertheless, current methodology suffers from several limitations, an important one being relatively low sensitivity in detecting fluorescently labeled targets on the chip arrays. Typically, targets in the range of picomolar concentrations or higher must be employed. Genetic analyses of natural targets in the attomolar or zeptomolar range therefore require target amplification by PCR. This procedure demands time and labor, and the target amplification can lead to errors in the sequence to be tested.

A need exits for a more sensitive, simpler, and cheaper detection method for polynucleotides arrayed on chips. Progress in detection technology has been made with the use of gold nanoparticle oligonucleotide conjugates as probes and signal amplification by silver ion reduction, which enables assays of polynucleotides of 50 fM concentration to be readily detected [for the methodology, see T. A. Taton, C. A. Mirkin; R. L. Letsinger, *Science,* 289, 1757 (2000). We describe here a discovery that significantly lowers further the target concentration required for assays employing gold nanoparticles and other metallic nanoparticles.

SUMMARY OF THE INVENTION

The present invention relates to a method for amplifying signal by enhancing the deposition of silver in detecting systems where the formation of a silver spot serves as a reporter for the presence of a molecule, including biological polymers (e.g., proteins and nucleic acids) and small molecules. The detecting systems include detection of molecules in situ (e.g., on cells or in a tissue sample) and assays where the molecule to be detected (the target molecule) is bound to a substrate or is captured by another molecule bound to a substrate (the capture molecule). The invention has special utility in increasing the signal strength in diagnostic and screening applications involving detection of target molecules arrayed at discrete positions on a solid surface. It, therefore, provides a means for greatly enhancing the sensitivity of tests carried out on microarrays or microchips. The process is distinguished by the simplicity and economy of its execution and the large enhancement in signal and, thereby, sensitivity realized.

This invention is based on the discoveries that (1) gold nanoparticles coated with oligonucleotides bind to silver that had previously been deposited on gold nanoparticle-oligonucleotide conjugates immobilized by hybridization on a glass substrate or plate and (2) that the resulting (gold nanoparticle-oligonucleotide-silver-(gold-oligonucleotide) structures function as catalyst for the further deposition of silver by reduction of silver ions. The first discovery is surprising since one might expect that the surface bound oligonucleotides, which shield the nanoparticles from non-specific binding to the glass surface and the oligonucleotides immobilized on the glass surface, would also shield the nanoparticles against interaction with the silver surface. Indeed, other work has shown that oligonucleotides protect gold nanoparticle oligonucleotide conjugates from fusing to form gold-gold bonds between individual nanoparticles even when the mixtures are dried. The second discovery is significant since it provides a means for substantially increasing the metallic mass at the site of the originally immobilized nanoparticles. In conjunction with development of buffer conditions that enable oligonucleotide nanoparticle conjugates that are unbound by hybridization or interaction with silver to be washed cleanly from the glass surface these findings opened opportunities for assaying polynucleotide targets at extremely low target concentrations.

Accordingly, one objective of the invention is to provide a method for amplifying a detection signal comprising:
 (a) providing a substrate having deposited silver;
 (b) contacting the substrate having deposited silver with a solution comprising nanoparticles having oligonucleotides bound thereto so as to produce a substrate having a nanoparticles-silver sandwich;
 (c) washing the substrate having said sandwich; and
 (d) contacting the substrate having said sandwich with silver ions and a reducing agent to promote silver deposition onto the nanoparticles of said sandwich.

The nanoparticles having oligonucleotides bound thereto comprise gold, silver, platinum or mixtures thereof. These nanoparticles may be in the form of gold nanoparticle-oligonucleotide conjugates or complexes.

Another object of the invention is to provide a method for promoting silver deposition onto a surface comprising silver, said method comprising the steps of:
 (a) providing a surface having silver bound thereto;
 (b) contacting the surface with a solution comprising nanoparticles having oligonucleotides bound thereto so as to produce a surface having a nanoparticles-silver sandwich;
 (c) washing the surface having said nanoparticles-silver sandwich;
 (d) contacting the surface having said nanoparticles-silver sandwich with a solution including silver ions under reducing conditions to promote silver deposition onto said nanoparticles of said nanoparticles-silver sandwich; and
 (e) washing the surface having deposited silver.

According to this method, the surface may include cells or tissue for in situ detection of target molecules. Preferably the nanoparticles having oligonucleotides bound thereto comprise gold nanoparticles having oligonucleotides bound thereto in conjugate or complex form. In practicing this invention, gold nanoparticle oligonucleotide conjugates are preferred.

A further object of the invention is to provide a kit for detection signal amplification comprising:
 (a) container including nanoparticles having oligonucleotides bound thereto;
 (b) container including a silver salt; and
 (c) container including a reducing agent.

The kit may include instructions for use in amplifying silver stain detection signals. Preferably the nanoparticles having oligonucleotides bound thereto comprise gold nanoparticles having oligonucleotides bound thereto in conjugate or complex form. In practicing this invention, gold nanoparticle oligonucleotide conjugates are preferred.

DESCRIPTION OF THE FIGURES

FIG. 2(b) shows the silver signal after one silver staining step followed by treatment with conjugate I and a second silver step.

FIG. 3(b) shows the same two spots from FIG. 3(a) after further development using nanoparticle-oligonucleotide complex III.

FIG. 5 illustrates a plate following application of the inventive signal amplification method of the invention. Spot obtained after two cycles of the nanoparticle-oligonucleotide (conjugate I)/silver staining amplification methodology applied when gold nanoparticle probes and an oligonucleotide target (63-mer) were immobilized on a glass plate. The concentration of the target oligonucleotide in this case was only 1 fM. The initial silver spot was not visible and amplification was achieved by two cycles of the gold nanoparticle (reagent I)/silver procedure.

DETAILED DESCRIPTION OF THE INVENTION

The present invention relates to a method for signal amplification for detecting target substances. In particular, the invention provides for amplification of signal and enhancement of assay sensitivity for detection of minute quantities of target molecules, e.g., nucleic acids, that are based on silver stain detection. In practicing this invention, the inventive method is used after the application of conventional silver staining where it leads to the formation of silver-gold(oligonucleotide)-silver assemblies, termed here silver-gold'-silver sandwich assemblies.

The prior steps leading up to and including conventional silver staining can, for example, involve: capture of a target oligonucleotide by an oligonucleotide capture probe bound to a glass surface, washing, addition of nanoparticle oligonucleotide conjugates complementary to an unhybridized segment of the bound target oligonucleotide, washing, addition of a silver staining solution (Ag+ plus a reducing agent, available through Sigma), washing, drying, and viewing, either with the naked eye or with aid of pictures obtained using a simple flat-bed scanner. This procedure was described by Taton et al., *Science,* 289, 1757 (2000), who showed that although the gold spot obtained was too weak to observe directly for target concentrations of 100 nM in oligonucleotide, conventional silver deposition affords a strong dark spot. The limit of detection for this system using conventional silver staining is 50 fM concentrations, for which an extremely faint spot is observed. Re-exposure to the silver solution did not noticeably further enhance the intensity of the spot.

For amplification of the silver signal by the inventive silver-gold'-silver sandwich method, the glass plate containing silver stain from a prior application of conventional staining is further exposed to an aqueous amplification solution of nanoparticles having oligonucleotides bound thereto, preferably gold nanoparticle-oligonucleotide conjugates or a gold-nanoparticle oligonucleotide complexes. The oligonucleotide sequence does not need to be related to the target oligonucleotide sequence or the sequences on the initial probes. For gold nanoparticle-oligonucleotide conjugates, the amplification solution generally contains between about 1 nM and about 5 nM nanoparticle oligonucleotide conjugates. The amplification solution may include salts, such as buffer salts, and detergents such as phosphate, citrate, HEPES, and NES and is preferably has a pH of about 7. In practicing the invention, an aqueous amplification solution including aqueous 0.1M NaCl and 10 mM phosphate (pH 7.0) was found to be particularly useful. For gold nanoparticle oligonucleotide complexes, the amplification solution is the same. Any suitable mode of exposing the silver stain to the amplification solution may be used. Representative examples include spraying, dipping, and the like.

After about 5 to 30 minutes, preferably about 10 minutes, the unbound nanoparticles conjugates or complexes are removed by washing the plate with a suitable aqueous solution, preferably water. Optionally, the plate is dried by any suitable method such as air drying. The plate is then re-exposed to a silver staining solution for a suitable time period, generally for about 5 to about 10 minutes, preferably about 5 minutes. It will be understood that any suitable silver staining method may be used. Suitable, but non-limiting, examples of useful silver staining methods and compositions are described, for instance, in M. A. Hayat, Ed., "Immunogold-Silver Staining," CRC Press (1995). Generally, silver staining solutions include silver ion in the form of a silver salt such as silver acetate (preferred), silver lactate, and silver nitrate. These solutions also include a reducing agent that is admixed into the solution just prior to use. Suitable, but non-limiting, examples of reducing agents include hydroquinone, n-propyl galate, p-phenylenediamine, and formaldehyde. If desired, other agents such as gum Arabic may be used to mediate the silver stain process. Any suitable mode of contacting the substrate with the silver stain solution may be used. Representative examples include spraying, dipping, and the like.

Following washing with water (preferred) or other suitable solution (e.g., aqueous solution containing 0.1M NaCl and 10 mM phosphate (pH 7.0) to remove unreacted silver stain solution, the re-exposed plate is observed visually or copied by a flat-bed scanner. This treatment leads to a great increase in the darkness of the spot. The process may be repeated as often as desired to further enhance the amount of deposited silver and the darkness of the spot. With this inventive amplification method, one can readily observe a dark silver spot for an assay using 25 fM target concentration. With two cycles of the new nanoparticle-silver sandwich procedure, 1 fM target solutions can be recognized, and with three cycles, 0.1 fM solutions give positive though weak spots. These experiments were carried out using 1 microliter of the target solution in each case. For the assay with 0.1 fM solution this corresponds to ~60 target molecules in the applied sample.

Any substrate can be used which allows observation of a silver stain as the detectable change. Suitable substrates include transparent solid surfaces (e.g., glass, quartz, plastics and other polymers. The substrate can be any shape or thickness, but generally will be flat and thin. Preferred are transparent substrates such as glass (e.g., glass slides) or plastics (e.g., wells of microtiter plates).

The silver stain signal amplification method of the invention depends on the use of nanoparticles-oligonucleotide conjugates or complexes that satisfy certain characteristics. First, the nanoparticles do not stick to the surface of the chip being tested. Ordinary nanoparticles prepared by the citrate reduction method of Frens (Frens, G., *Nat. Phys. Sci.,* 241, 20–22 (1973) are not satisfactory since they bind indiscriminately to the oligonucleotide-derivatized glass plate used as the substrate for these assays. Subsequent silver enhancement then gives false positives as dark areas. Second, the nanoparticles bind to a deposited silver surface such that on subsequent washing, the attached nanoparticles remain bound to the silver area while nanoparticles suspended in solution are cleanly removed. Third, the nanoparticles function as agents to reduce silver ions under silver staining conditions. In practicing this invention, useful nanoparticles are nanoparticles coated with oligonucleotides linked through sulfur to the surface (nanoparticle oligonucleotide conjugates) such as the ones described in J. J. Storhoff et al., *J. Am. Chem. Soc.,* 120, 1958 (1999) (for a specific example, see conjugate I in Example 1 below) or with natural type oligonucleotides adsorbed to the surface (nanoparticle oligonucleotide complexes) such as conjugate III described in Example 1. Both types of nanoparticles work well in low or moderate salt solution (e.g. up to 0.1 M), but the conjugates containing the sulfur anchor are particularly preferred for tests conducted at high salt concentration, at which the complexes formed by simple adsorption of oligonucleotides are unstable and aggregate. It will be understood by the ordinary skilled artisan that any nanoparticle preparation that meets the criteria listed above are useful as intermediary agents in forming the sandwich assemblies, and the methodology can be applied for the amplification of the silver signal for any target visualized by an initial silver deposition. While gold nanoparticles are particularly preferred, any nanoparticle that catalyze the reduction of silver can be used including silver and platinum nanoparticles.

The preparation of nanoparticles suitable for use in the practice of the invention, the attachment of oligonucleotides to them, the flatbed scanner technique, and various assays formats for the detection of nucleic acids using conventional silver staining are described in co-pending applications Ser. Nos. 09/760,500, filed Jan. 12, 2001; 09/603,830, filed Jun. 26, 2000; 09/344,667, filed Jun. 25, 1999; 09/240,755, filed Jan. 29, 1999; 60/031,809, filed Jul. 29, 1996; 60/176,409; and 60/200,161, filed Apr. 26, 2000; and international application Nos. PCT/US97/12783, filed Jul. 21, 1997; PCT/US00/17507, filed Jun. 26, 2000; and PCT/US01/01 190, filed Jan. 12, 2001, entitled "Nanoparticles Having Oligonucleotides Attached Thereto And Uses Therefor," the entire contents of which are incorporated herein by reference.

EXAMPLES

Example 1

Preparation of Oligonucleotide Modified Gold Nanoparticles

Oligonucleotides and 5'-mercaptoalkyl-oligonucleotid were prepared using phosphoramidite chemistry as described by Storhoff et al. [*J. Am. Chem. Soc.* 120, 1959–1964 (1998)]. Gold nanoparticles (~13 nm diameter) were prepared as described by Grabar, K. C., et al. [*J. Analyt. Chem.*, 67, 735–743 (1995); Frens, G., *Nat. Phys. Sci.*, 241, 20–22 (1973)].

For preparation of the nanoparticle conjugate (I) used in the sandwich silver-gold'-silver amplification scheme, 5'-mercaptoalkyl-oligonucleotide II was prepared and joined to gold nanoparticles by the general linking procedure described by Storhoff et al., [*J. Am. Chem. Soc.* 120, 1959–1964 (1998)]. The nanoparticle-oligonucleotide complex (III) was prepared by mixing 1 μL of an aqueous solution containing 0.26 $A_{260}$ Units of oligonucleotide IV with 100 μL of citrate stabilized gold colloid (prepared as described by Grabar et al. [*J. Analyt. Chem.*, 67, 735–743 (1995)) and allowing the solution to stand overnight.

I. Conjugate formed from gold nanoparticles and II.
II. 5'-HS(CH$_2$)$_6$OP(O)(O )O-(A)$_{20}$TGGGTAGCAGACCTC (SEQ ID NO.:1)
III. Complex formed from gold nanoparticles and IV
IV. 5'-GCTCTAGAATGAACGGTGGAAGGCGGCAGG (SEQ ID NO.:2)

Example 2

Sandwich Amplification of Silver Signal

In this Example, four separate experiments were conducted using the nanoparticle oligonucleotide conjugate (I) or complex (III) prepared as described in Example 1, and glass slides containing silver spots from oligonucleotide assays carried out using the silver staining method described by T. A. Taton et al, *Science*, 289, 1757–60 (2000). The glass plate bearing the silver spots was exposed to a solution of gold nanoparticle conjugate I (FIGS. 2, 4, and 5) or gold nanoparticle complex III (FIG. 3) for 10 minutes, washed with 1 M NaNO$_3$ in nanopure water, and exposed for five minutes at room temperature to a 1:1 mixture of freshly mixed sample of the two commercial Silver Enhancer solutions (Catalog Nos. 55020 and 55145, Sigma Corporation, St. Louis, Mo.) for 5 minutes, following the Sigma protocol for the silver staining step, including final washes with nanopure water, sodium thiosulfate solution, and nanopure water. The plate was dried and observed, both visually and by copying for records using a Hewlett Packard Scanner [Model no. 5200C]. The direct visual observations of spots corresponded to the prints obtained using the scanner. The figures are enlarged.

Figure 1:
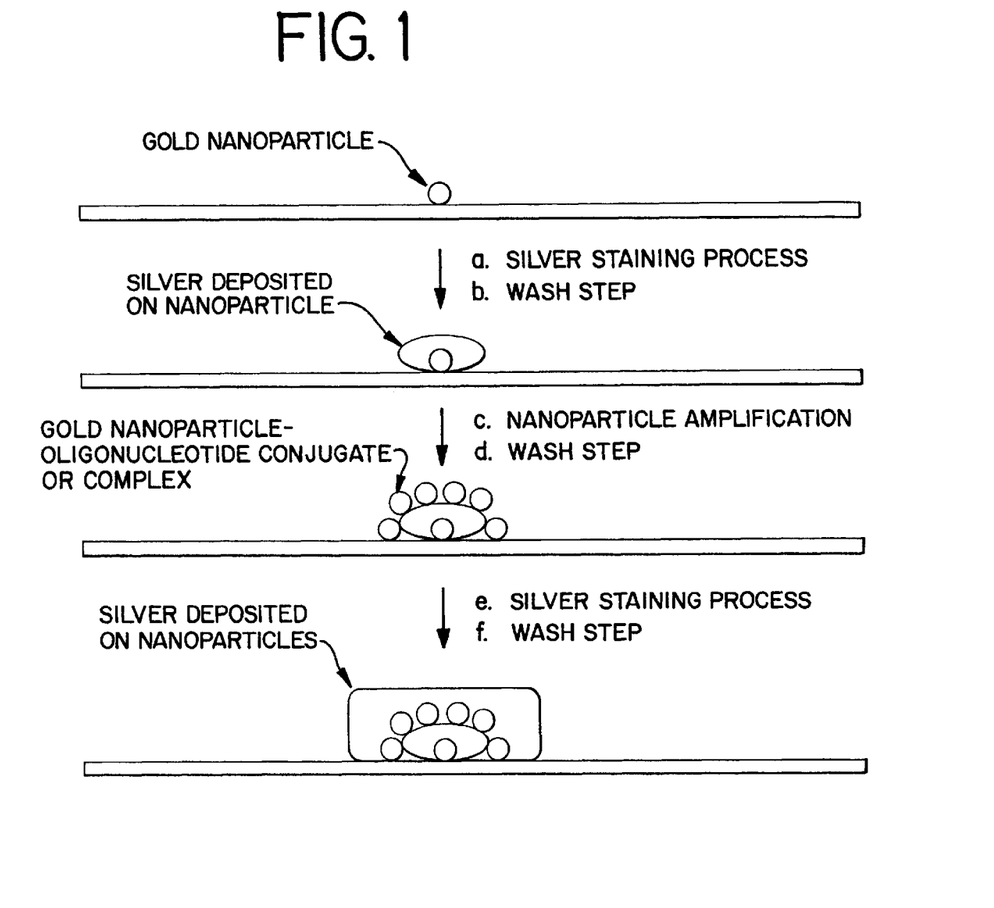
FIG. 1 is a schematic representation of amplification of a detection signal for a gold nanoparticle immobilized on a solid surface. Step "a" is conventional silver staining. In step "c", gold nanoparticles bearing oligonuclotides are bound to the silver surface. Step "e" is conventional silver staining of the gold nanoparticles that were bound to the previous silver surface.
Figure 2A:
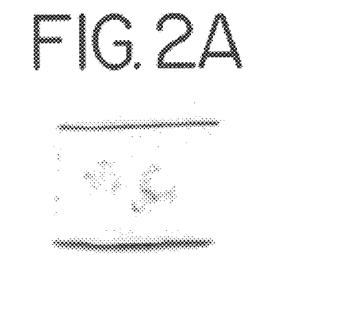
FIGS. 2(a) and (b) illustrate two plates with or without application of the amplification method of the invention. The plate shown in FIG. 2(a) was subjected to a second round of conventional silver staining in an attempt to further enhance the spot. Slight but very little signal enhancement took place. The plate shown in FIG. 2(b) was subjected to the signal amplification method of the invention.
Figure 2B:
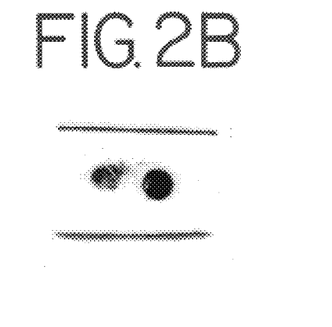

FIG. 2 illustrates the results for the first experiment using nanoparticle oligonucleotide conjugate I. In this experiment, two plates, each containing very faint silver spots from previous hybridization and silver staining of a dilute target solution, were used. Plate (a) was subjected to a second round of conventional silver staining in an attempt to further enhance the spot. Slight but very little signal enhancement took place. Plate (b) was subjected to conditions for the gold sandwich amplification. This entailed exposing the plate containing the weak silver spots to the solution of nanoparticle conjugate I for 10 minutes, followed by washing with water and conventional silver staining for 4 minutes. The darkness of the spots in plate (b) relative to those in plate (a) clearly demonstrate the power of the new metal sandwich or signal enhancement method.

Figure 3A:
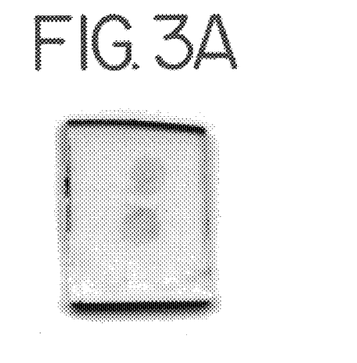
FIGS. 3(a) and (b) illustrate two plates with or without application of the amplification method of the invention. The plate shown in FIG. 3(a) indicates the signal obtained for a sample using conventional silver staining. Two spots are shown from a conventional silver staining step on a very dilute DNA sample. The plate shown in FIG. 3(b) shows the enhancement achievable by the application of the inventive signal amplification method.
Figure 3B:
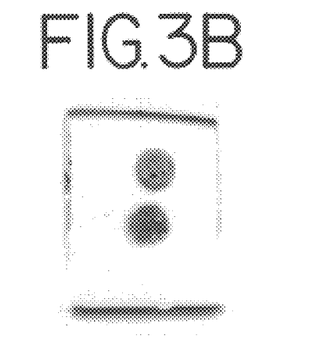

FIG. 3 illustrates the results for an experiment using nanoparticle oligonucleotide complex III. Plate (a) indicates the signal obtained for a sample using conventional silver staining. Plate (b) shows the enhancement achievable by the gold sandwich technology. Note that two sample spots are shown in each case. For plate (b), a plate containing a weak silver spot corresponding to that in plate (a) was exposed to a solution of nanoparticle oligonucleotide complex III, and following washing, was subjected to conventional silver staining. In this case, three parts of colloid III, prepared as described above, was mixed with seven parts of 10 mM phosphate buffer at pH 7. The plate was then exposed to this colloid solution for 10 minutes, washed with nanopure water, and exposed to the silver staining mixture for 4 minutes as before.

Figure 4A:
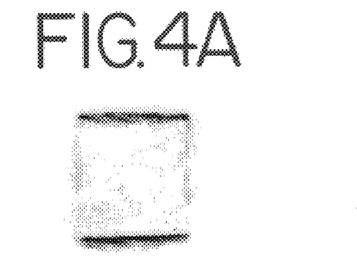
FIGS. 4(a) and (b) illustrate two plates with or without application of the amplification method of the invention. The plate shown in FIG. 4(a) shows the results of conventional silver staining for a test in which a 25 fM solution of the target oligonucleotide was used. The plate shown in FIG. 4(b) shows the results for the same test in which the initial silver staining was followed with the signal amplification method of the invention. The spot shown in 4(b) was obtained for silver-gold-silver procedure where the gold reagent is conjugate I.
Figure 4B:
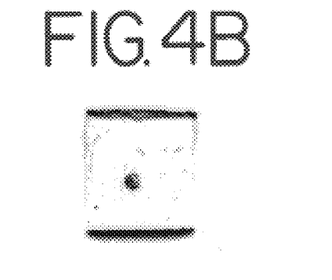

FIG. 4 illustrates the results for an experiment using gold nanoparticle oligonucleotide I to enhance the weak silver signal resulting from an assay of a 63 nucleotide target oligonucleotide 5' GTA GGC GAA CCC TGC CCA GGT CGA CAC ATA GG T GAG GTC TGC TAC CCA CAG CCG GTT AGG TGC 3' (SEQ ID NO.: 3) at 25 fM concentration. Note that our standard assay using just silver amplification gives a very weak spot (plate (a)). Plate (a) shows the results of conventional silver staining for a test in which a 25 fM solution of the target oligonucleotide was used. Plate (b) shows the results for the same test in which the initial silver staining was following by 10 minute exposure to the colloidal solution of nanoparticle conjugate I, followed by silver staining. In this case, the gold solution had been diluted six-fold with 0.1 M NaCl-10 mM phosphate buffer. Note the strong signal for a target, captured at 25 fM concentration, after the metal sandwich enhancement procedure.

Figure 5:
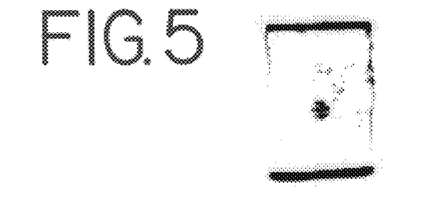

FIG. 5 illustrates the results for an experiment using nanoparticle oligonucleotide conjugate I to enhance the silver signal obtained from an assay carried out using a 63-mer target [see SEQ ID NO.: 3] at a concentration of 1 fM. In this case, our standard procedure for silver staining failed to show any spot. Double enhancement using the gold-silver treatment, however, showed a strong signal, as shown. This experiment was carried out by treating the plate that had been exposed to silver amplification by the stand procedure successively with: (1) gold nanoparticle conjugate I (1.5 nM in nanoparticles in 0.1 M NaCl and 10 mM phosphate buffer at pH 7.0) for 10 minutes; (2) wash with 1 M NaNO$_3$; (3) treat with a mixture of Silver Enhancer solutions (catalog nos. 5020 and S 5145, Sigma Corporation, by the Sigma protocol; (4) wash with 1 M sodium nitrate; (5) repeat steps 1–4; (6) wash with sodium thiosulfate ; and (7) wash with water.

What we claim:

1. A method for amplifying a signal comprising:
   (a) providing a substrate having deposited silver;
   (b) contacting the substrate having deposited silver with a solution comprising nanoparticles having oligonucleotides bound thereto so as to produce a substrate having a nanoparticles-silver sandwich;
   (c) washing the substrate having said sandwich;
   (d) contacting the substrate having said sandwich with silver ions and a reducing agent to promote silver deposition onto the nanoparticles of said sandwich; and
   (e) washing the substrate having the silver-nanoparticles-silver-sandwich.

2. The method according to claim 1, wherein the nanoparticles comprise gold, silver, platinum or mixtures thereof.

3. The method according to claim 1, wherein the nanoparticles comprise gold nanoparticle-oligonucleotide conjugates or complexes.

4. The method according to claim 1, wherein the silver ion is derived from a silver salt comprising silver acetate, silver lactate, or silver nitrate.

5. The method according to claim 1, wherein the reducing agent comprises hydroquinone, n-propyl galate, p-phenylenediamine, or formaldehyde.

6. The method according to claim 1, wherein step (b) contacting is performed for a period ranging from about 5 to 30 minutes.

7. The method according to claim 6, wherein step (b) contacting is performed for about 10 minutes.

8. The method according to claim 1, wherein step (d) contacting is performed for a period ranging from about 5 to 10 minutes.

9. The method according to claim 8, wherein step (d) contacting is performed for about 5 minutes.

10. The method according to claim 1, wherein the deposited silver bound to the substrate is arranged in the form of an array.

11. The method according to claim 1, wherein step (c) washing is performed with water.

12. The method according to claim 1, wherein the substrate is glass.

13. A method for promoting silver deposition onto a surface comprising silver, said method comprising the steps of:
   (a) providing a surface having silver bound thereto;
   (b) contacting the surface with a solution comprising nanoparticles having oligonucleotides bound thereto so as to produce a surface having a nanoparticles-silver sandwich;
   (c) washing the surface having said nanoparticles-silver sandwich;
   (d) contacting the surface having said nanoparticles-silver sandwich with a solution including silver ions under reducing conditions to promote silver deposition onto said nanoparticles of said nanoparticles-silver sandwich; and (e) washing the surface of step (d), said surface having deposited silver.

14. The method according to claim 13, wherein said surface comprises cells or tissue.

15. The method according to claim 13, wherein the nanoparticles comprise gold, silver, platinum or combinations thereof.

16. The method according to claim 13, wherein the nanoparticles having oligonucleotides bound thereto comprise gold nanoparticles having oligonucleotides bound thereto.

17. The method according to claim 13, wherein the nanoparticles comprise gold nanoparticle-oligonucleotide conjugates or complexes.

18. The method according to claim 13, wherein the silver ion is derived from a silver salt comprising silver acetate, silver lactate, or silver nitrate.

19. The method according to claim 13, wherein the reducing agent comprises hydroquinone, n-propyl galate, p-phenylenediamine, or formaldehyde.

20. The method according to claim 13, wherein step (b) contacting is performed for a period ranging from about 5 to 30 minutes.

21. The method according to claim 20, wherein step (b) contacting is performed for a period of about 10 minutes.

22. The method according to claim 13, wherein step (d) contacting is performed for a period ranging from about 5 to 10 minutes.

23. The method according to claim 22, wherein step (d) contacting is performed for about 5 minutes.

24. The method according to claim 13, wherein the silver bound to the substrate are arranged in the form of an array.

25. A kit for signal amplification comprising:

(b) container including nanoparticles having oligonucleotides bound thereto;

(b) container including a silver salt; and (c) container including a reducing agent.

26. The kit according to claim 25, wherein the nanoparticles comprise gold, silver, platinum or combinations thereof.

27. The kit according to claim 26, wherein the nanoparticles comprising gold nanoparticles having oligonucleotides bound thereto.

28. The kit according to claim 25, wherein the nanoparticles comprise gold nanoparticle-oligonucleotide conjugates or complexes.

29. The kit according to claim 25, wherein the silver salt comprises silver acetate, silver lactate, or silver nitrate.

30. The kit according to claim 25, wherein the reducing agent comprises hydroquinone, n-propyl galate, p-phenylenediamine, or formaldehyde.

* * * * *

UNITED STATES PATENT AND TRADEMARK OFFICE
CERTIFICATE OF CORRECTION

PATENT NO. : 6,602,669 B2
DATED : August 5, 2003
INVENTOR(S) : Robert L. Letsinger and Viswanadham Garimella It is certified that error appears in the above-identified patent and that said Letters Patent is hereby corrected as shown below:

Column 1,
Line 7, please insert -- This application was supported by a grant from the National Institutes of Health, grant number GM57356. The U.S. government may have certain rights to this invention. --.
Line 25, please delete "immunochemitry" and insert therefor -- immunochemistry --.

Column 2,
Line 34, please delete "exits" and insert therefor -- exists --.
Line 41, please delete "(2000)" and insert therefor -- (2000)] --.

Column 6,
Line 62, please delete "catalyze" and insert therefor -- catalyzes --.
Line 66, please delete "assays" and insert therefor -- assay --.

Column 7,
Line 18, please delete "oligonucleotid" and insert therefor -- oligonucleotide --.

Column 12,
Line 7, please delete "are" and insert therefor -- is --.
Line 9, please delete "(b)" and insert -- (a) --.

Signed and Sealed this

Eighth Day of June, 2004

JON W. DUDAS
*Acting Director of the United States Patent and Trademark Office*